United States Patent
Yin

(10) Patent No.: US 10,818,039 B2
(45) Date of Patent: Oct. 27, 2020

(54) IMAGE PROCESSING METHOD, IMAGE PROCESSING DEVICE AND MEDICAL IMAGING DEVICE

(71) Applicant: BOE TECHNOLOGY GROUP CO., LTD., Beijing (CN)

(72) Inventor: Xinshe Yin, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 79 days.

(21) Appl. No.: 16/319,953

(22) PCT Filed: Apr. 9, 2018

(86) PCT No.: PCT/CN2018/082325
§ 371 (c)(1),
(2) Date: Jan. 23, 2019

(87) PCT Pub. No.: WO2018/214655
PCT Pub. Date: Nov. 29, 2018

(65) Prior Publication Data
US 2019/0251705 A1    Aug. 15, 2019

(30) Foreign Application Priority Data

May 22, 2017    (CN) .......................... 2017 1 0364198

(51) Int. Cl.
*G06T 7/90*     (2017.01)
*G16H 30/40*   (2018.01)
*G06T 5/00*     (2006.01)

(52) U.S. Cl.
CPC ............... *G06T 7/90* (2017.01); *G06T 5/009* (2013.01); *G16H 30/40* (2018.01); *G06T 2207/30004* (2013.01)

(58) Field of Classification Search
CPC . G06T 7/90; G06T 5/009; G06T 2207/30004; G06T 2207/10024;
(Continued)

(56) References Cited

U.S. PATENT DOCUMENTS 5,345,315 A  *  9/1994  Shalit ................... H04N 1/4078
                                                              347/3
2005/0207641 A1*  9/2005  Bala ................... H04N 1/40012
                                                              382/162
(Continued)

FOREIGN PATENT DOCUMENTS

CN          1394327 A     1/2003
CN        101097584 A     1/2008
(Continued)

OTHER PUBLICATIONS

PCT International Search Report, Application No. PCT/CN2018/082325, dated Jun. 28, 2018, 5 pages: with English translation.
(Continued)

*Primary Examiner* — Nimesh Patel
(74) *Attorney, Agent, or Firm* — Armstrong Teasdale LLP

(57) ABSTRACT

Embodiments of the present disclosure provide an image processing method, an image processing device, and a medical imaging device. The image processing method includes acquiring color image data, and generating grayscale image data based on the color image data. Luminance of a grayscale image represented by the grayscale image data is equivalent to luminance of a color image represented by the color image data. The image processing device includes an image acquisition unit configured to acquire color image data, and a processor configured to generate grayscale image data based on the color image data. The medical imaging device includes the image processing device described above, and a displayer configured to display an image according to the image data generated by the
(Continued)

image processing device. Embodiments of the present disclosure may conveniently convert a color image into a grayscale image and improve display definition of the medical imaging device.

14 Claims, 3 Drawing Sheets

(58) Field of Classification Search
CPC ............ G06T 7/11; G06T 2207/10076; G06T 2207/20072; G06T 2207/30242; G06T 7/136; G06T 2207/30044; G06T 2207/30056; G06T 2207/30081; G06T 2207/30084; G06T 7/62; G06T 11/60; G06T 7/0021; G06T 2207/30061; G06T 2207/30096; G06T 2207/10081; G06T 7/246; G06T 11/001; G06T 2207/20021; G06T 2207/10116; G06T 2207/10136; G06T 2207/30016; G06T 2207/30068; G06T 7/174; G06T 7/0012; G06T 2207/20216; G06T 2207/10004; G06T 11/00; G06T 1/0007; G06T 2207/20036; G06T 15/00; G06T 19/20; G06T 2207/20084; G06T 2210/41; G06T 2219/2012; G06T 3/0093; G06T 5/00; G06T 7/00; G06T 7/001; G16H 30/40; G16H 30/20; H04N 1/40012; H04N 1/60; H04N 5/2258; H04N 5/238; H04N 5/265; H04N 9/69; H04N 9/73; H04N 9/3182; H04N 17/02; H04N 1/00127; H04N 1/00129; H04N 1/644; H04N 9/64; H04N 1/465; H04N 1/6027; H04N 9/315; G09G 2360/16; G09G 2320/0666; G09G 2320/0242; G09G 3/2003; G09G 2320/0673; G09G 2320/0693; G09G 3/3607; G09G 5/02; G09G 2320/0626; G09G 2340/06; G09G 2360/145; G09G 2300/0452; G09G 2320/0233; G09G 3/3611; G09G 2320/0271; G09G 3/3406; G09G 1/285; G09G 3/20; G09G 2300/0465; G09G 2320/0606; G09G 2370/08; G09G 3/3258; G09G 3/3413; G09G 2380/08; G09G 3/2092; G09G 5/003; G09G 5/026; G09G 2300/0443; G09G 2320/062; G09G 2320/103; G09G 2320/02; G09G 2320/0238; G09G 2320/041; G09G 3/2077; G02F 1/133528; G02F 1/133602; G02F 1/29; G02F 1/292; G02F 2001/291; G02F 2201/305; G02F 2201/44; G02F 1/133514; G02F 1/13624; G02F 2001/134345; G02F 2201/52; G02F 1/133603; G02F 1/133621; H01L 27/3216; H01L 27/3218; H01L 27/3244; H01L 51/5281; H01L 51/5275; G06K 2209/05; G06K 9/4652; G06K 9/4671; G06K 9/0014; G01J 2005/0077; G01J 3/0208; G01J 3/2823; G01J 3/45; G01J 3/36; G01J 5/02; G01J 5/089; G01J 5/0896; A61B 10/0233; A61B 2017/3411; A61B 2017/3413; A61B 2090/374; A61B 2090/378; A61B 8/4416; A61B 8/5238; A61B 90/10; A61B 5/015; A61B 1/00006; A61B 1/00009; A61B 1/00016; A61B 1/0005; A61B 1/05; A61B 5/0077; A61B 5/01; A61B 5/055; G01S 3/8034; G01S 7/64; G01S 7/52071; H01S 5/34333; H01S 5/4043; H01S 5/4093; G06F 3/0484; G06F 3/04842; G06F 3/04845; G06F 3/0488; G06F 3/04886; G06F 3/1415; G06F 3/011

See application file for complete search history.

(56) References Cited

U.S. PATENT DOCUMENTS

| | | | | |
|---|---|---|---|---|
| 2008/0137148 | A1* | 6/2008 | Oh | H04N 1/40012 358/3.23 |
| 2009/0195486 | A1* | 8/2009 | Moldvai | G09G 5/06 345/88 |
| 2010/0208985 | A1* | 8/2010 | Lee | H04N 1/40012 382/163 |
| 2013/0016901 | A1* | 1/2013 | Iwaki | H04N 9/68 382/162 |
| 2014/0314317 | A1* | 10/2014 | Min | G06T 11/001 382/167 |
| 2015/0022569 | A1* | 1/2015 | Iguchi | G09G 3/3406 345/697 |
| 2015/0097856 | A1 | 4/2015 | Sasaki | |
| 2016/0350940 | A1* | 12/2016 | Wang | G06T 7/90 |

FOREIGN PATENT DOCUMENTS

| | | |
|---|---|---|
| CN | 101197918 A | 6/2008 |
| CN | 102629466 A | 8/2012 |
| CN | 102708554 A | 10/2012 |
| CN | 104484659 A | 4/2015 |
| CN | 104992404 A | 10/2015 |
| CN | 105574854 A | 5/2016 |
| CN | 107169937 A | 9/2017 |

OTHER PUBLICATIONS

PCT Written Opinion, Application No. PCT/CN2018/082325, dated Jun. 28, 2018, 6 pages: with English translation of relevant part.
China First Office Action, Application No. 201710364198.5, dated Jun. 5, 2019, 19 pps.: with English translation.

\* cited by examiner

IMAGE PROCESSING METHOD, IMAGE PROCESSING DEVICE AND MEDICAL IMAGING DEVICE

CROSS REFERENCE TO RELATED APPLICATIONS

This patent application is a National Stage Entry of PCT/CN2018/082325 filed on Apr. 9, 2018, which claims the benefit and priority of Chinese Patent Application No. 201710364198.5 filed on May 22, 2017, the disclosures of which are incorporated by reference herein in their entirety as part of the present application.

BACKGROUND

The present disclosure relates to the field of image processing, and in particular, to an image processing method, an image processing device and a medical image device.

With the wide use of display technology in various fields, the requirements on display technology are also diverse. For example, in the medical field, diagnostic technologies such as x-ray digital radiography (DR), x-ray computer radiography (CR), and x-ray computed tomography (CT) have developed rapidly, and displayers have gradually replaced films as the main tool for imaging diagnosis.

In general, during imaging diagnosis, it is necessary to present a black and white image to a doctor at last, so as to reduce the interference of chromatic aberration. Existing universal color displayers do not fully adapt to the requirements for displaying black and white images, and often the display is unclear. However, dedicated black and white displayers tend to be costly, and difficult to be used widely.

BRIEF DESCRIPTION

The present disclosure provides an image processing method, an image processing device, and a medical imaging device.

A first aspect of the present disclosure provides an image processing method including acquiring color image data, and generating grayscale image data based on the color image data such that luminance of a grayscale image represented by the grayscale image data is equivalent to luminance of a color image represented by the color image data.

In embodiments of the present disclosure, the color image data includes RGB data. The RGB data includes an R value, a G value, and a B value of a pixel. Generating grayscale image data based on the color image data includes generating luminance data based on the RGB data, and generating grayscale image data based on the luminance data. The luminance data includes a luminance value of the pixel. A grayscale value of the pixel corresponds to the luminance value.

In embodiments of the present disclosure, generating luminance data based on the RGB data includes calculating the luminance value of the pixel using a formula: $L=A1*R+A2*G+A3*B$. R represents the R value of the pixel, G represents the G value of the pixel, and B represents the B value of the pixel. A1, A2, and A3 represent predetermined calculation coefficients. L represents the luminance value of the pixel.

In embodiments of the present disclosure, generating grayscale image data according to the luminance data includes setting the luminance value of the pixel to the grayscale value.

In embodiments of the present disclosure, the image processing method further includes adjusting a color temperature of the grayscale image.

In embodiments of the present disclosure, adjusting the color temperature of the grayscale image includes setting an R value, a G value, and a B value of the pixel according to the grayscale value of the pixel in the grayscale image data, wherein the R value=G value=B value, and adjusting the R value, the G value, and the B value according to a predetermined color temperature.

In embodiments of the present disclosure, setting the R value, the G value, and the B value of the pixel according to the grayscale value of the pixel includes setting the R value=G value=B value=grayscale value.

In embodiments of the present disclosure, adjusting the R value, the G value, and the B value according to the predetermined color temperature includes acquiring a lookup table corresponding to the predetermined color temperature, and adjusting the R value, the G value, and the B value according to the lookup table.

A second aspect of the present disclosure provides an image processing device including an image acquisition unit configured to acquire color image data, a processor configured to generate grayscale image data based on the color image data, such that luminance of a grayscale image represented by the grayscale image data is equivalent to luminance of a color image represented by the color image data.

In embodiments of the present disclosure, the color image data includes RGB data, and the RGB data includes an R value, a G value, and a B value of a pixel. The processor is configured to generate luminance data based on the RGB data when generating grayscale image data based on the color image data, wherein the luminance data includes a luminance value of the pixel, and generate grayscale image data based on the luminance data, wherein a grayscale value of the pixel corresponds to the luminance value.

In embodiments of the present disclosure, the processor is configured to, when generating luminance data based on the RGB data, calculate the luminance value of the pixel using a formula: $L=A1*R+A2*G+A3*B$, wherein R represents the R value of the pixel, G represents the G value of the pixel, and B represents the B value of the pixel, A1, A2, and A3 represent predetermined calculation coefficients, and L represents the luminance value of the pixel.

In embodiments of the present disclosure, the processor is configured to, when generating grayscale image data according to the luminance data, set the luminance value of the pixel to the grayscale value.

In embodiments of the present disclosure, the processor is further configured to adjust a color temperature of the grayscale image.

In embodiments of the present disclosure, the processor is configured to, when adjusting the color temperature of the grayscale image, set an R value, a G value, and a B value of the pixel according to the grayscale value of the pixel in the grayscale image data, wherein the R value=G value=B value, and adjust the R value, the G value, and the B value according to a predetermined color temperature.

In embodiments of the present disclosure, the processor is configured to, when setting the R value, the G value, and the B value of the pixel according to the grayscale value of the pixel, set the R value=G value=B value=grayscale value.

In embodiments of the present disclosure, the processor is configured to, when adjusting the R value, the G value, and the B value according to the predetermined color temperature, acquire a lookup table (LUT) corresponding to the predetermined color temperature, and adjust the R value, the G value, and the B value according to the lookup table.

In embodiments of the present disclosure, the processor is further configured to adjust a color temperature of the grayscale image.

A third aspect of the present disclosure provides a medical imaging device including the image processing device described above, and a displayer configured to display an image according to the image data generated by the image processing device.

Embodiments of the present disclosure may convert a color image acquired by the medical imaging device into the grayscale image.

BRIEF DESCRIPTION OF THE DRAWINGS

In order to illustrate the technical solutions of the embodiments of the present disclosure more clearly, the drawings of the embodiments will be briefly described below, and it should be appreciated that the drawings described below are only related to some of the embodiments of the present disclosure, rather than limiting the present disclosure, in which.

DETAILED DESCRIPTION

The specific embodiments of the present disclosure are described in detail below with reference to the accompanying drawings, but are not to be construed as limiting.

It should be understood that various modifications may be made to the embodiments disclosed herein. Therefore, the description should not be taken as limiting, but merely as examples of the embodiments. Those skilled in the art may also achieve other modifications within the scope and spirit of the present disclosure.

The accompanying drawings, which are included in and constitute part of the description, illustrate embodiments of the present disclosure and, together with the general description of the disclosure given above and the detailed description of the embodiments given below, explain the principles of the disclosure.

These and other features of the present disclosure will become apparent from the following description of example forms of the embodiments given as non-limiting examples with reference to the accompanying drawings.

It should also be understood that, although the present disclosure has been described with reference to some specific examples, those skilled in the art may certainly realize many other equivalent forms of the disclosure, which have features as claimed and are therefore within the scope of protection defined by these features.

In conjunction with the drawings, the above and other aspects and features of the present disclosure will become more apparent in view of the following detailed description.

The specific embodiments of the present disclosure are described hereinafter with reference to the drawings; however, it is understood that the disclosed embodiments are only examples of the present disclosure, which may be implemented in various manners. Well-known and/or repeated functions and structures are not described in detail so as not to obscure the present disclosure with unnecessary or extra details. Therefore, the specific structural and functional details disclosed herein are not intended to be limiting, but are merely used as a basis and representative basis of the claims to teach one skilled in the art to use the disclosure in any substantially suitable detailed structure in many ways.

The description may use the phrases "in an embodiment", "in another embodiment", "in yet another embodiment" or "in other embodiments", which may refer to one or more of the same or different embodiments according to the present disclosure.

The embodiments of the present disclosure are described in detail below with reference to the accompanying drawings, and provide an image processing method, an image processing device, and a medical imaging device.

Figure 1:
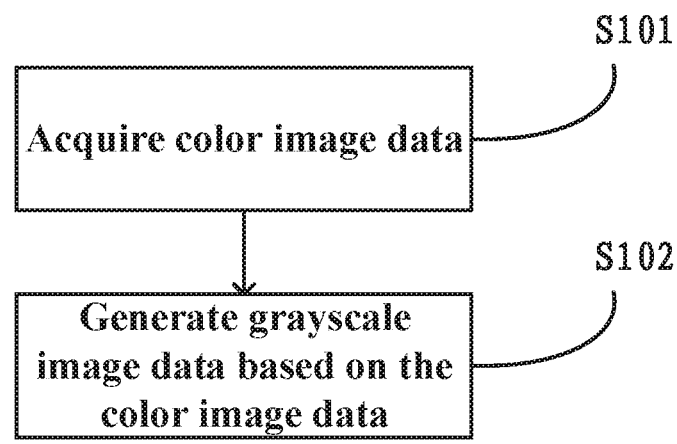
FIG. 1 is an exemplary flowchart of an image processing method provided in embodiments of the present disclosure.

FIG. 1 is an exemplary flowchart of an image processing method provided in embodiments of the present disclosure.

As shown in FIG. 1, the image processing method includes step S101, acquiring color image data, and step S102, generating grayscale image data based on the color image data. Luminance of a grayscale image represented by the grayscale image data is equivalent to luminance of a color image represented by the color image data. The grayscale image data includes a grayscale value of the pixel, and the grayscale value of the pixel may be an arbitrary numerical value for indicating the grayscale level. In general, grayscale values may be taken from an integer range of 0 to 255 to represent different grayscale levels. The full white corresponds to 255, and the full black corresponds to 0. As the value changes from 0 to 255, the pixel exhibits a gradual change from black to white.

In the embodiments of the present disclosure, after the color image data has been acquired, it is converted into grayscale image data, which may be conveniently displayed on different types of displayers.

Figure 2:
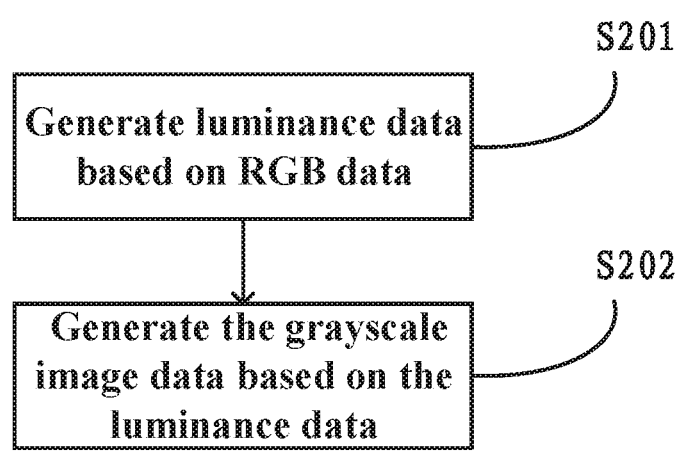
FIG. 2 is an exemplary flowchart of the sub-steps of step S102 of FIG. 1.

FIG. 2 is an exemplary flowchart of the sub-steps of step S102 of FIG. 1.

Color image data may have a variety of different formats, and these formats are also referred to as color spaces. For example, the color image data may use various formats such as three primary colors RGB (red, green, and blue), YUV (luminance, red color difference, and blue color difference). In the YUV format, luminance data Y is provided directly. That is, the color image data may include the luminance value of the pixel, and in such a case, the grayscale image data may be obtained directly using the luminance value. In embodiments of the present disclosure, the grayscale value of the pixel may be made equal to the luminance value of the pixel.

In the three primary color RGB image data format, luminance data is not directly provided. The color image data includes the R value, G value, and B value of the pixel, and the luminance value of the pixel needs to be extracted from the RGB. As shown in FIG. 2, at this time, step S102 may include step S201 of generating luminance data based on the RGB data, and step S202 of generating grayscale image data according to the luminance data. The grayscale value of the pixel corresponds to the luminance value.

In the embodiments of the present disclosure, the processor may first perform data analysis on the acquired color image, and acquire RGB values of each pixel in the image, namely respectively the R value, G value, and B value, calculate a luminance value of each pixel according to the acquired RGB values, and acquire a grayscale image of equivalent luminance based on the calculated luminance value.

In addition, in the embodiments of the present disclosure, step S201 includes calculating the luminance value of the pixel using a formula: L=A1*R+A2*G+A3*B. R represents the R value of the pixel, G represents the G value of the pixel, and B represents the B value of the pixel. A1, A2, and A3 represent predetermined calculation coefficients. L represents the luminance value of the pixel.

That is to say, for each pixel's RGB values, the equivalent luminance value may be obtained through the above conversion model. The above-mentioned respective coefficients A1, A2, and A3 may be adjusted according to actual needs. In the embodiments of the present disclosure, the above A1 may be 0.299, A2 may be 0.578, and A3 may be 0.114. At the same time, the sum of the above A1, A2, and A3 may be about 1.

Such grayscale image data is suitable for display on a black-and-white displayer or a general-purpose color displayer, and the grayscale value is equal to the luminance value, which is advantageous for display clarity of the color displayer device, thereby facilitating viewing and analysis by the user.

For the case other than the RGB format, since corresponding conversion relationships exist for these different formats, the image processing method may further include a conversion step to convert other formats into the RGB format, and then perform the above processing.

Figure 3:
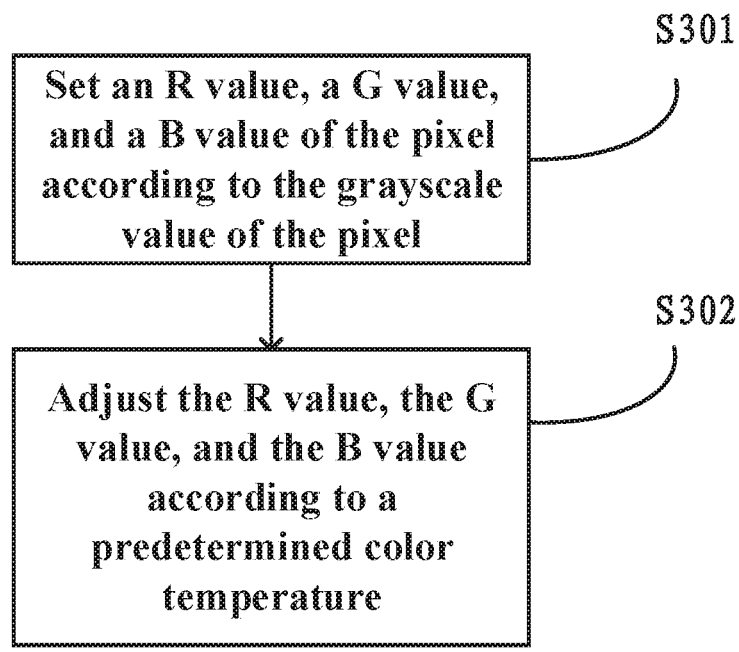
FIG. 3 shows other illustrative steps of the image processing method of FIG. 1.

FIG. 3 shows other illustrative steps of the image processing method of FIG. 1.

Grayscale images may need to be represented in different scenes. For example, an application scenario of a medical displayer may include a conference room, a diagnostic room, an operating room, etc., and these different scenarios may require grayscale images to exhibit different color temperature effects. In order to obtain display effects in different color temperature environments, the color temperature of the grayscale image may be adjusted. As shown in FIG. 3, adjusting the color temperature of the grayscale image may include step S301 of setting an R value, a G value, and a B value of the pixel according to the grayscale value of the pixel in the grayscale image data, and step S302 of adjusting, according to a predetermined color temperature, the R value, G value, and B value.

In step S301, it is desirable to make the image luminance displayed on the display based on the color data signal inputted according to S201 equal to the luminance of the grayscale image data displayed on the display. For one pixel, its R value, G value, and B value may be set to be the same to present a grayscale image without color. Further, it is possible to directly set the R value=G value=B value=grayscale value. At this time, the R value, the G value, and the B value may be directly used for display on a color displayer to obtain a grayscale image. At the same time, the luminance value is recalculated using the formula in step S201: L=A1*R+A2*G+A3*B, and R=G=B, A1+A2+A3=1, then, L=R=G=B. Thus, in this way, it can be ensured that the luminance of the grayscale image remains unchanged. That is, only by adjusting the R value, the G value, and the B value, it is possible to display a grayscale image on the same color displayer without changing the luminance.

In embodiments of the present disclosure, the R value, the G value, and the B value may be further adjusted. Adjustments may bring additional effects to the following applications, such as color temperature correction.

Specifically, in step S302, the R value, the G value, and the B value may also be adjusted while considering the predetermined color temperature. Color temperature is a parameter used to characterize the chromaticity of a light source. It is defined as if the color of the light emitted by a light source (i.e., light color, also known as chromaticity) is the same as the color of the light emitted by a black body at a certain temperature, the absolute temperature value of the black body is called the color temperature of the light source, color temperature in short. Displaying the same image at different color temperatures may provide the user with different viewing experiences. For example, for white color displayed likewise, white light with a low color temperature looks biasing to red, while white light with a high color temperature looks biasing to blue. Such changes may also be reflected in minor adjustments of the Rout value, the Gout value, and the Bout value. The difference in the degree of adjustment may be reflected by the change in the coefficients stored in the lookup table.

The pre-stored lookup table (LUT) is used in the process of color temperature correction. For an input value of the grayscale image R=G=B, the corresponding coefficients are found in the lookup table, and the predetermined input value is calculated to obtain modified Rout, Gout, Bout values. The modified Rout, Gout, and Bout values are used for the input of the display, and different color temperature effects of the corresponding grayscale levels may be obtained to improve the viewing experience of the user in different color temperature environments.

Step S302 may specifically include acquiring a lookup table corresponding to a predetermined color temperature, and adjusting an R value, a G value, and a B value according to the lookup table. By storing multiple lookup tables, the input values ultimately inputted to the display may be adjusted for different color temperatures. For example, corresponding to color temperatures of 4500K, 6500K, or 9300K, different lookup tables are stored. Such an adjustment causes the modified R value, G value, and B value inputted to the display to produce minor changes in the vicinity of the grayscale value L for tuning the viewing experience of the image slightly and highlighting different detail features. The specific coefficients in the lookup table may be set according to the application environment by theoretical calculation or experimental method. Table 1 shows an example of a specific lookup table. In the table, the required modified R value, G value, and B value corresponding to the grayscale value at a predetermined color temperature are directly stored. For a specific value, if it is necessary to represent an image with a low color temperature, the R value may be increased. For example, it is possible to make $R_n > n$, wherein n represents any grayscale value. If it is necessary to represent an image with a high color temperature, the B value may be increased. For example, it is possible to make $B_n > n$, wherein n represent any grayscale value. In the implementation of the present disclosure, after the R value, the G value, and the B value have been adjusted to coincide with the grayscale value, it is only necessary to use the grayscale value to perform a retrieval in the lookup table as shown in Table 1 at a predetermined color temperature, that is, the modified R value, G value, and B value may be obtained at the same time, without a complicated calculation process or multiple different lookup tables corresponding to different color components. The embodiments of the present disclosure provide a fast, practical color temperature adjustment process.

TABLE 1

R value, G value, and B value lookup table
at a predetermined color temperature

| Grayscale value inputted L | Rout R-LUT | Gout G-LUT | Bout B-LUT |
|---|---|---|---|
| 0 | R0 | G0 | B0 |
| 1 | R1 | G1 | B1 |
| 2 | R2 | G2 | B2 |
| 3 | R3 | G3 | B3 |
| ... | ... | ... | ... |
| 253 | R253 | G253 | B253 |
| 254 | R254 | G254 | B254 |
| 255 | R255 | G255 | B255 |

Figure 4:
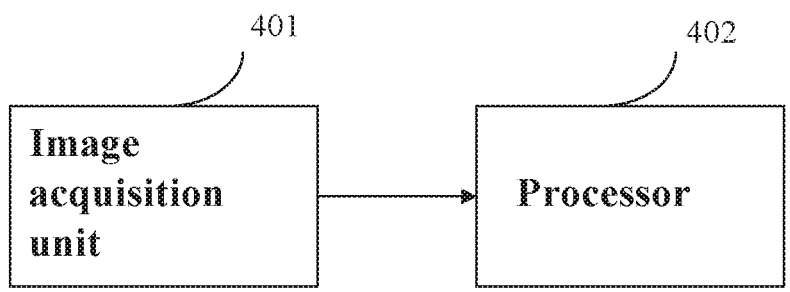
FIG. 4 is an exemplary block diagram of an image processing device provided in embodiments of the present disclosure.

FIG. 4 is an exemplary block diagram of an image processing device provided in embodiments of the present disclosure.

As shown in FIG. 4, the image processing device includes an image acquisition unit 401 configured to acquire color image data, and a processor 402 configured to generate grayscale image data based on the color image data.

The image processing device may be a device having a computing function, such as a personal computer or an embedded system. The image acquisition unit 401 may acquire image data from an external device through various serial or parallel data interfaces, for example, from a DR device, a CR device, a CT device, a color ultrasound machine, an ultrasound diagnostic instrument, and the like. For example, the image acquisition unit 401 may acquire color image data including RGB data. The processor 402 may be a central processing unit (CPU), a micro computing unit (MCU), a field programmable logic gate array (FPGA), etc., for implementing the image processing method described above.

As a specific example, the processor 402 may perform the following steps: step S201 of generating luminance data based on RGB data, wherein a luminance value of the pixel is calculated using a formula: $L=A1*R+A2*G+A3*B$, step S202 of generating grayscale image data according to the luminance data, wherein the grayscale value is equal to the luminance value, step S301 of setting the R value, the G value, and the B value of the pixel according to the grayscale value of the pixel, wherein the R value=G value=B value=grayscale value, and step S302 of adjusting, according to a predetermined color temperature, the R value, the G value, and the B value, wherein the coefficient used in the adjustment is obtained from the corresponding lookup table (LUT).

Figure 5:
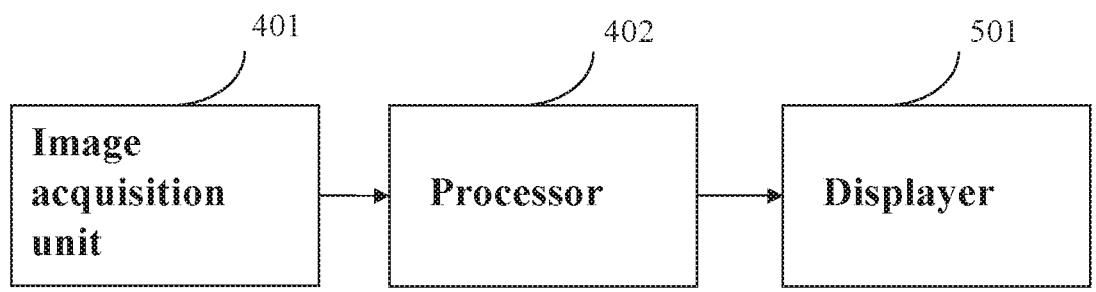
FIG. 5 is an exemplary block diagram of a medical imaging device provided in embodiments of the present disclosure.

FIG. 5 is an exemplary block diagram of a medical imaging device provided in embodiments of the present disclosure.

As shown in FIG. 5, the medical imaging device includes the above-described image processing device. The medical imaging device also includes a displayer 501 configured to display an image according to the image data generated by the image processing device.

The medical imaging device may apply the image processing method applied in the medical imaging device as described in the above embodiments. In the embodiments of the present disclosure, the medical imaging device may include a digital imaging device such as a DR, CR, CT, etc., but is not limited thereto. The embodiments of the present disclosure may realize that when the medical image device described acquires a color image, the medical image device can conveniently convert the color image into a grayscale image for display, thereby conveniently and clearly representing the physical condition of the patient through the grayscale image.

Through the above configuration, the embodiments of the present disclosure may realize the adjustment of the image color temperature, that is, under different color temperature requirements, the corresponding color temperature may be adaptively adjusted to meet different user requirements.

The medical imaging device in the embodiments of the present disclosure may acquire a color image, convert the color image acquired by the medical imaging device into a grayscale image, ensure the clarity of the grayscale image, facilitate the viewing of the medical image, and solve the problem that the effect achieved by the color displayer when showing a black and white image is not good.

The above embodiments are merely exemplary embodiments of the present disclosure, and are not intended to limit the disclosure, and the scope of the disclosure is defined by the claims. A person skilled in the art may make various modifications or equivalents to the present disclosure within the spirit and scope of the disclosure, and such modifications or equivalents are also considered to be within the scope of the disclosure.

What is claimed is:

1. An image processing method comprising:
    acquiring color image data; and
    generating grayscale image data based on the color image data;
    wherein a luminance of a grayscale image represented by the grayscale image data is equivalent to a luminance of a color image represented by the color image data;
    wherein the color image data comprises RGB data, and wherein the RGB data comprises an R value, a G value, and a B value of a pixel; and
    wherein generating grayscale image data based on the color image data comprises:
        generating luminance data based on the RGB data, wherein the luminance data comprises a luminance value of the pixel; and
        generating the grayscale image data based on the luminance data, wherein a grayscale value of the pixel corresponds to the luminance value;
    wherein generating luminance data based on the RGB data comprises:
        calculating the luminance value of the pixel using a formula: $L=A1*R+A2*G+A3*B$;
        wherein R represents the R value of the pixel, G represents the G value of the pixel, B represents the B value of the pixel, A1, A2, and A3 represent predetermined calculation coefficients, and L represents the luminance value of the pixel.

2. The image processing method according to claim 1, wherein generating the grayscale image data according to the luminance data comprises setting the luminance value of the pixel to the grayscale value.

3. The image processing method according to claim 1, further comprising adjusting a color temperature of the grayscale image.

4. The image processing method according to claim 3, wherein adjusting the color temperature of the grayscale image comprises:
    setting an R value, a G value, and a B value of the pixel according to the grayscale value of the pixel in the grayscale image data, wherein the R value=G value=B value; and
    adjusting the R value, the G value, and the B value according to a predetermined color temperature.

5. The image processing method according to claim 4, wherein setting the R value, the G value, and the B value of the pixel according to the grayscale value of the pixel comprises setting the R value=G value=B value=grayscale value.

6. The image processing method according to claim 4, wherein adjusting the R value, the G value, and the B value according to the predetermined color temperature comprises:
acquiring a lookup table (LUT) corresponding to the predetermined color temperature; and
adjusting the R value, the G value, and the B value according to the lookup table.

7. An image processing device comprising:
an image acquisition unit configured to acquire color image data; and
a processor configured to generate grayscale image data based on the color image data;
wherein a luminance of a grayscale image represented by the grayscale image data is equivalent to luminance of a color image represented by the color image data
wherein the color image data comprises RGB data, and wherein the RGB data comprises an R value, a G value, and a B value of a pixel; and
wherein the processor is configured to:
generate luminance data based on the RGB data when generating grayscale image data based on the color image data, wherein the luminance data comprises a luminance value of the pixel; and
generate the grayscale image data according to the luminance data, wherein the grayscale value of the pixel corresponds to the luminance value;
wherein the processor is configured to, when generating luminance data based on the RGB data, calculate the luminance value of the pixel using a formula: L=A1*R+A2*G+A3*B;
wherein R represents the R value of the pixel, G represents the G value of the pixel, B represents the B value of the pixel, A1, A2, and A3 represent predetermined calculation coefficients, and L represents the luminance value of the pixel.

8. The image processing device according to claim 7 NOR wherein the processor is configured to, when generating grayscale image data according to the luminance data, set the luminance value of the pixel to the grayscale value.

9. The image processing device according to claim 7, wherein the processor is further configured to adjust a color temperature of the grayscale image.

10. The image processing device according to claim 9, wherein the processor is configured to, when adjusting the color temperature of the grayscale image, i) set an R value, a G value, and a B value of the pixel according to the grayscale value of the pixel in the grayscale image data, wherein the R value=G value=B value, and ii) adjust the R value, the G value, and the B value according to a predetermined color temperature.

11. The image processing device according to claim 10, wherein the processor is configured to, when setting the R value, the G value, and the B value of the pixel according to the grayscale value of the pixel, set the R value=G value=B value=grayscale value.

12. The image processing device according to claim 10, wherein the processor is configured to, when adjusting the R value, the G value, and the B value according to the predetermined color temperature, acquire a lookup table (LUT) corresponding to the predetermined color temperature, and adjust the R value, the G value, and the B value according to the lookup table.

13. A medical imaging device comprising:
the image processing device according to claim 7; and
a displayer configured to display an image according to the image data generated by the image processing device.

14. The medical imaging device according to claim 13, wherein the processor is configured to, when generating the grayscale image data according to the luminance data, set the luminance value of the pixel to the grayscale value.

* * * * *

UNITED STATES PATENT AND TRADEMARK OFFICE
CERTIFICATE OF CORRECTION

PATENT NO. : 10,818,039 B2
APPLICATION NO. : 16/319953
DATED : October 27, 2020
INVENTOR(S) : Xinshe Yin Page 1 of 1

It is certified that error appears in the above-identified patent and that said Letters Patent is hereby corrected as shown below:

In the Claims

In Claim 7, Column 9, Line 21, delete "image data" and insert therefor -- image data; --.
In Claim 8, Column 10, Lines 3-4, delete "claim 7 NOR wherein" and insert therefor -- claim 7, wherein --.

Signed and Sealed this
Fifteenth Day of December, 2020

Andrei Iancu
*Director of the United States Patent and Trademark Office*